United States Patent [19]
Iwamoto et al.

[11] Patent Number: 5,759,583
[45] Date of Patent: Jun. 2, 1998

[54] SUSTAINED RELEASE POLY (LACTIC/ GLYCOLIC) MATRICES

[75] Inventors: Taro Iwamoto, Cupertino, Calif.; Akio Kimura, Utsunomiya, Japan; Takehiko Ohyama, Hino, Japan; Yasuyuki Takahashi, Sagamihara, Japan

[73] Assignee: Syntex (U.S.A.) Inc., Palo Alto, Calif.

[21] Appl. No.: 560,081

[22] Filed: Nov. 17, 1995

[51] Int. Cl.⁶ ............................. A61K 9/50; A61K 47/30
[52] U.S. Cl. ...................... 424/502; 424/501; 514/772.3
[58] Field of Search ................................. 424/489, 501, 424/502; 514/772.3

[56] References Cited

U.S. PATENT DOCUMENTS

| | | | |
|---|---|---|---|
| 4,675,189 | 6/1987 | Kent et al. | 424/490 |
| 5,594,091 | 1/1997 | Igari et al. | 528/271 |

FOREIGN PATENT DOCUMENTS 88-210210
[30] 12/1986 European Pat. Off.
2 127 689 4/1984 United Kingdom.

OTHER PUBLICATIONS

Asano et al., "In Vivo Characteristics of Low Molecular Weight Copoly(L–Lactice Acid/Glycolic Acid) Formulations with Controlled Release of Luteinizing Hormone–Releasing Hormone Agonist", *J. Controlled Release*, 9:111–112 (1989).

Kitchell et al., "Poly(lactic/glycolic acid) Biodegradable Drug–Polymer Matrix Systems", *Methods in Enzymology*, vol. 112, 436–448.

Sanders et al., "Prolonged Controlled–Release of Nafarelin, a Luteinizing Hormone–Releasing Hormone Analogue, From Biodegradable Polymeric Implants: Influence of Composition and Molecular Weight of Polymer", *J. Pharm. Sci.* 1986, (75)4:356–360.

Heya et al., "Effects of counteranion of TRH and loading amount on control of TRH release from copoly(dl–lactic/ glycolic acid) microspheres prepared by an in–water drying method", *Int. J. Pharm.*, 69(1991)69–75.

Sturesson et al., "Preparation of biodegradable poly(lactic– co–glycolic) acid microspheres and their in vitro release of timolol maleate", *Int. J. Pharm.*, 89(1993)235–244.

*Primary Examiner*—Carlos Azpuru
*Attorney, Agent, or Firm*—Heller Ehrman White & McAuliffe

[57] ABSTRACT

This invention provides a sustained release composition comprising a PLGA matrix, a bioactive agent, and a quaternary ammonium surfactant, in which the release profile of the bioactive agent from the PLGA matrix is controlled by the concentration of the quaternary ammonium surfactant.

16 Claims, 3 Drawing Sheets

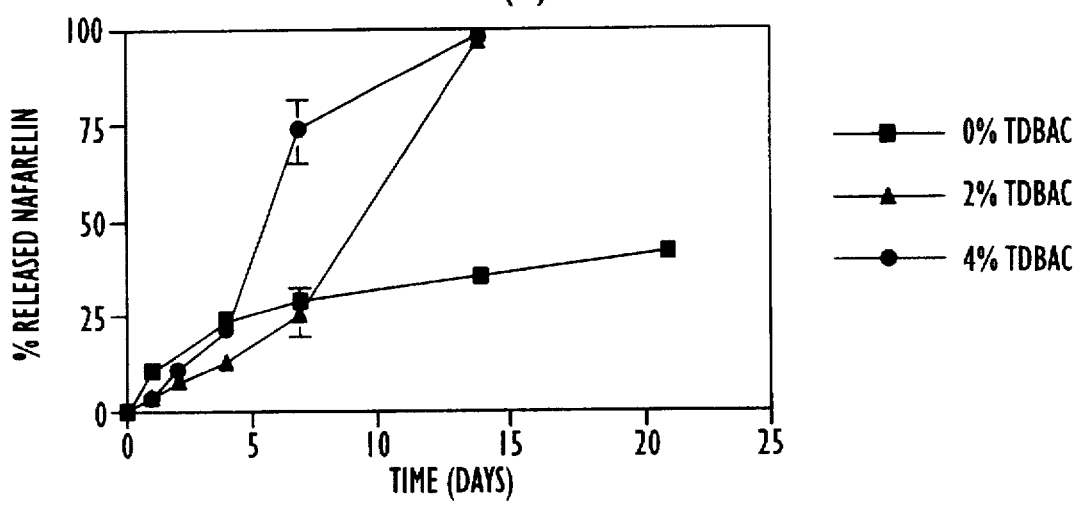
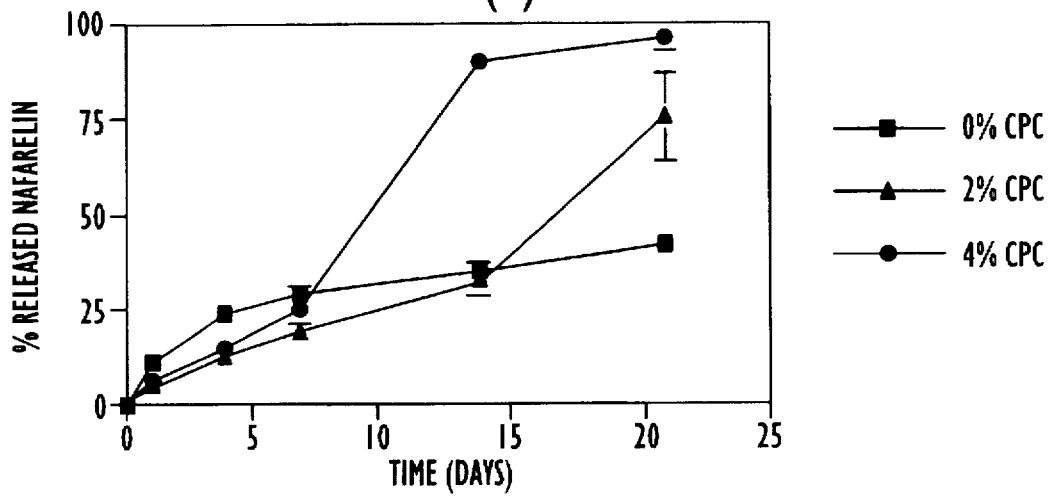
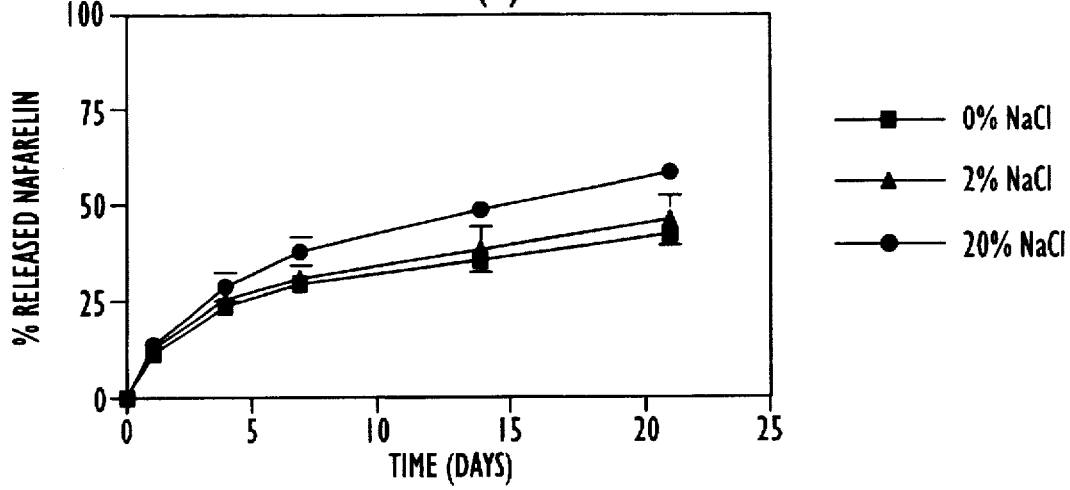

SUSTAINED RELEASE POLY (LACTIC/GLYCOLIC) MATRICES

BACKGROUND OF THE INVENTION

1. Field of the Invention

This invention relates to sustained release delivery systems, in particular poly(lactic/glycolic acid) (PLGA) delivery systems for the sustained release of bioactive agents.

2. Description of Related Art

Poly(lactic/glycolic acid) (PLGA) has been used as a non-toxic biodegradable matrix for long-acting drug delivery of pharmaceutical agents (see, for example U.S. Pat. No. 4,675,189). The mechanism of release of drugs from PLGA appears to depend on both diffusion through the polymer matrix and degradation of the polymer (Shah et al., *J. Controlled Release*, 18:261–270 (1992)). The degradation rate of PLGA can be controlled by varying the molecular weight or the molar ratio of the two monomers in the polymer (Sanders et al., *J. Pharm. Sci.*, 75:356–360 (1986)). Attempts have been made to improve the drug release profiles not only by controlling the physical properties of PLGA but also by using additives. For example, relatively hydrophilic compounds such as lactide (Ogawa et al., *Chem. Pharm. Bull.*, 36:1502–1507 (1988)) and polyethylene glycol (Sturesson et al., *Int. J. Pharm.*, 89:235–244 (1993)) have been added to PLGA matrices with the aim of providing more aqueous channels, followed by rapid drug release. However, neither system showed continuous in vitro release.

The effect of additives upon the release profile of poly (lactic acid) (PLA) matrices has also been reported. The addition of tributyl citrate or glycerin as a plasticizer significantly increased the initial permeability of PLA membrane (Pitt et al., *J. Biomed. Mater. Res.*, 13:497–507 (1979)). Bodmeier et al. have shown that although the water soluble salt, sodium chloride, simply increased the initial drug release rate (Bodmeier et al., *J. Pharm. Sci.*, 78:819–822 (1989)), a blend of low molecular weight PLA accelerated total drug release (Bodmeier et al., *Int. J. Pharm.*, 51:1–8 (1989)).

SUMMARY OF THE INVENTION

This invention provides a sustained release composition comprising a PLGA matrix, a bioactive agent, and a quaternary ammonium surfactant, in which the release profile of the bioactive agent from the PLGA matrix is controlled by the concentration of the quaternary ammonium surfactant.

BRIEF DESCRIPTION OF THE DRAWINGS

FIG. 1 Cumulative release profile of nafarelin acetate from PLGA cylinders, with (A) TDBAC; (B) CPC; or (C) NaCl.

DETAILED DESCRIPTION OF THE INVENTION

Definitions

Figure 2A:
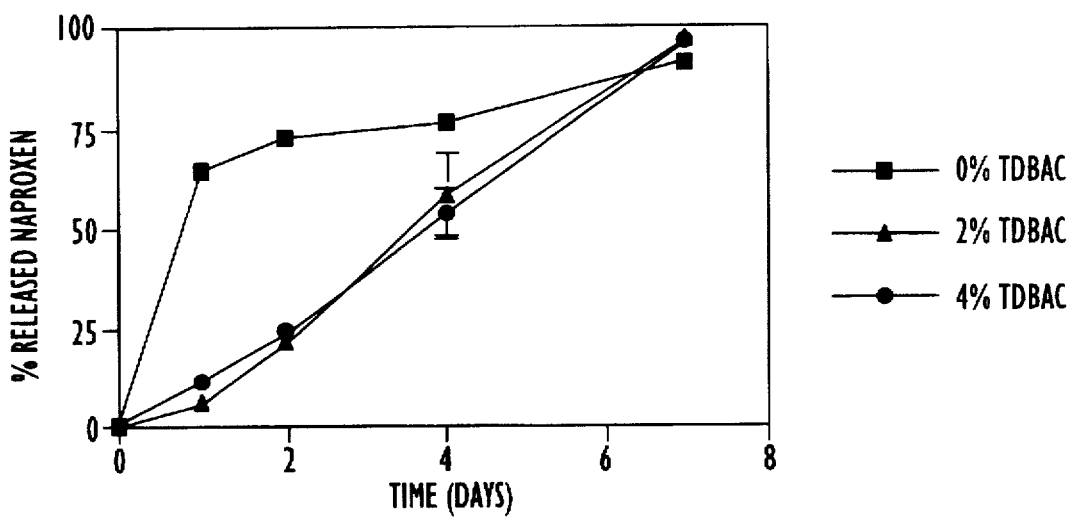
FIG. 2 Cumulative release profile of naproxen from PLGA cylinders, with (A) TDBAC or (B) NaCl.

Poly(lactic/glycolic) acid (PLGA) refers to a copolymer of lactic and glycolic acid, generally having a molecular weight up to about 50,000. The ratio of L:G is from about 100:0 to about 25:75. Additional comonomers and/or additives, such as plasticizers and stabilizers, may be present provided that such optional elements do not adversely impact upon the release of the bioactive agent from the PLGA matrix.

A bioactive agent is a synthetic or natural compound which demonstrates a biological effect when introduced into a living creature. Such agents may include diagnostic and therapeutic agents including both large and small molecules intended for the treatment of acute or chronic conditions. The only limitation upon the agent is that it exhibit adequate efficacy for its intended use after incorporation into the PLGA matrix.

A quaternary ammonium surfactant is a salt of a nitrogenous cation in which a central nitrogen atom is bonded to four organic radicals and an anion, of general formula $R_4N^+X^-$ which exhibits surface active properties. Such materials may be categorized as detergents, wetting agents, or emulsifiers. In a quaternary ammonium surfactant generally at least one of the R groups is a long chain (greater than 6 carbon atoms) alkyl or aryl group. Representative quaternary ammonium surfactants include, but are not limited to, those of the alkylammonium, benzalkonium, and pyridinium families. More specifically, the quaternary ammonium surfactants are selected from alkyltrimethylammonium salts, alkyldimethylbenzylammonium salts, and alkylpyridinium and imidazolium salts.

Sustained (or controlled) release refers to the gradual release of bioactive agent from the PLGA matrix over a period of time. While there may be an initial burst phase, it is preferred that the release display relatively linear kinetics, thereby providing a constant supply of bioactive agent over the release period. The release period may vary from several hours to several months, depending upon the bioactive agent and its intended use. It is desirable that the cumulative release of the bioactive agent from the matrix over the treatment period be relatively high to avoid the need for excessive loading of the matrix and consequent waste of unreleased bioactive agent. The duration of the release period may be controlled by, inter alia, the mass and geometry of the matrix, the concentration of active agent, the locus of administration, the molecular weight and molar composition of the matrix, and, as demonstrated herein, the addition of release profile modifying agents.

The incorporation of the bioactive agent and the release modifying agent into the PLGA matrix may be accomplished by any of various techniques known to the skilled artisan. Such techniques include, but are not limited to, the microencapsulation technologies disclosed in U.S. Pat. Nos. 4,675,189 and 4,954,298, melt extrusion processes as exemplified herein, and melt pressing as described in *J. Controlled Release*, 9:111–122 (1989). The geometry of the matrix (e.g. cylinder, microsphere, fiber) will of course be dictated by the fabrication technique and will affect the concomitant release kinetics; however, it is expected that the current invention will be operable regardless of matrix geometry.

The concentration of bioactive agent will vary depending upon the agent, its intended use, i.e. short or long duration, and the method of fabrication. In the embodiment described herein, the active agent concentration is from about 0.1% to about 20% by weight, preferably from about 1% to about 10% by weight, most preferably from about 2% to about 6% by weight. The concentration of quaternary ammonium surfactant will also vary depending upon the agent, the matrix, the desired release profile, and the like. In the embodiment described herein the quaternary ammonium surfactant concentration is from about 0.5% to about 15% by weight, preferably from about 2% to about 8% by weight.

To exemplify the invention three bioactive agents of differing physical properties were examined: nafarelin acetate, a medium molecular weight, water-soluble peptide (MW=1322), naproxen, a low molecular weight, water insoluble compound (MW=230) and ketorolac tromethamine, a low molecular weight, water soluble compound (MW=376). These bioactive agents were melt blended with two representative quaternary ammonium surfactants: tetradecyldimethylbenzylammonium chloride (TDBAC) and cetylpyridinium chloride (CPC). Sodium chloride was used to prepare comparative, bioactive agent-containing PLGA matrices.

Cylinders including the bioactive agents (drugs) at a concentration of 4% by weight and the surfactants at various concentrations were prepared from PLGA's with weight-average molecular weights of 4,500 to 18,000 by the melt-extrusion method without the use of organic solvents.

PLGA's, with copolymer ratio of lactic acid/glycolic acid of 50/50 and weight-average molecular weights of 4,500, 10,000 and 18,000, respectively (abbreviated as PLGA-4, 500, PLGA-10,000 and PLGA-18,000) were purchased from Taki Chemical Co., Ltd.; tetradecyldimethylbenzylammonium chloride (TDBAC), from Nippon Oil & Fats Co., Ltd.; and cetylpyridinium chloride (CPC), from Wako Pure Chemical Ind. Other chemicals were of reagent grade.

The molecular weight of PLGA was measured on a Shimadzu HPLC system (6A), columns: Waters ultrastyragel $10^2$, $10^3$ and $10^4$ Å; mobile phase: THF; flow rate: 1.0 ml/min.; wavelength: 230 nm; standard: polystyrene (Supelco Inc., molecular weight range of 760–90,000).

EXAMPLE 1

This Example demonstrates that quaternary ammonium salts can modify the release profile of water soluble, medium molecular weight peptide drugs from PLGA matrices.

Cylinders containing 4% by weight nafarelin acetate (Syntex, Palo Alto, CA) in PLGA-4,500 without additive and with (by weight) 2% TDBAC, 4% TDBAC, 2% CPC, 4% CPC, 2% NaCl, or 20% NaCl were prepared as described below. A mixture (200 mg) of drug with PLGA and the selected amount of surfactant was placed in a glass tube and heated at a melt temperature of 75° C. to melt the polymer. The melt was mixed homogeneously, charged into a polypropylene syringe and extruded. A cylinder 1.3 mm in diameter was obtained, cut into 5 mm lengths, and the drug content and the molecular weight of PLGA determined to confirm their stabilities during the preparation process, by high performance liquid chromatography (HPLC), as described below. The recovery of nafarelin from the cylinder was more than 90% and the molecular weight of the PLGA remained unaltered.

Nafarelin was extracted from the PLGA cylinder in a mixed solution of acetonitrile and potassium phosphate aqueous solution (23:77) and assayed by HPLC, column: Wakosil C8, 4.6 mm×25 cm; mobile phase: 0.1M $NH_4H_2PO_4CH_3CN$ (72:25:25); flow rate: 1.0 ml/min.; wavelength: 225 nm.

Drug release properties were studied at 37° C. using a rotating bottle apparatus. A cylinder was put into a glass bottle containing 5 ml of 0.2M phosphate buffer, pH 7.0. The medium was replaced by a fresh one at specified times and analyzed for the released drug by HPLC under the same conditions as described above.

FIG. 1 shows the release profiles in vitro of nafarelin from the PLGA cylinders (MW=4,500) with the different additives; (A): TDBAC, (B): CPC and (C): sodium chloride, respectively. Nafarelin release from the PLGA cylinder without additive was significantly sustained and followed the matrix release mechanism suggested by Higuchi (1963), i.e., the cumulative percentage of nafarelin released was proportional to the square root of time (correlation coefficient; r=0.985). For 21 days in the release test, the total percentage of nafarelin released was limited to 42%. However, the nafarelin release from the PLGA cylinder with TDBAC or CPC as an additive was much more constant without leveling off for the entire test period and was accelerated depending on the amount of the additive used. The cylinders with TDBAC (2% and 4%) showed the complete release of nafarelin during 14 days. On the other hand, the percentage of nafarelin released from the cylinder with CPC (2%) was approximately 75% for 21 days. Since the molecular weights of TDBAC and CPC are similar (368 and 340, respectively), it appears that TDBAC surpasses CPC with regard to accelerating nafarelin release from PLGA matrices. The addition of sodium chloride (2% and 20%) to the PLGA cylinder did not significantly change the nafarelin release profile.

EXAMPLE 2

This Example demonstrates that quaternary ammonium salts can modify the release profiles of low molecular weight, water insoluble drugs, from PLGA matrices.

Cylinders containing 4% by weight naproxen (Syntex, Palo Alto, Calif.) in PLGA-10,000 without additive and with (by weight) 2% TDBAC, 4t TDBAC, 4% NaCl, or 8% NaCl. were prepared as described below. A mixture (200 mg) of drug with PLGA and the selected amount of surfactant was placed in a glass tube and heated at a melt temperature of 80° C. to melt the polymer. The melt was mixed homogeneously, charged into a polypropylene syringe and extruded. A cylinder 1.3 mm in diameter was obtained, cut into 5 mm lengths, and the drug content and the molecular weight of PLGA determined to confirm their stabilities during the preparation process, by high performance liquid chromatography (HPLC), as described below. The recovery of naproxen from the cylinder was more than 90% and the molecular weight of the PLGA remained unaltered.

Naproxen was extracted from the PLGA cylinder in a mixed solution of acetonitrile and potassium phosphate aqueous solution (23:77) and assayed by HPLC, column: Spherisorb C18, 4.6 mm×25 cm; mobile phase: $CH_3OH$—$H_2O$—$CH_3COOH$ (55:44:1); flow rate: 0.8 ml/min.; wavelength: 254 nm.

Drug release properties were studied at 37° C. using a rotating bottle apparatus. A cylinder was put into a glass bottle containing 5 ml of 0.2M phosphate buffer, pH 7.0. The medium was replaced by a fresh one at specified times and analyzed for the released drug by HPLC under the same conditions as described above.

Figure 2B:
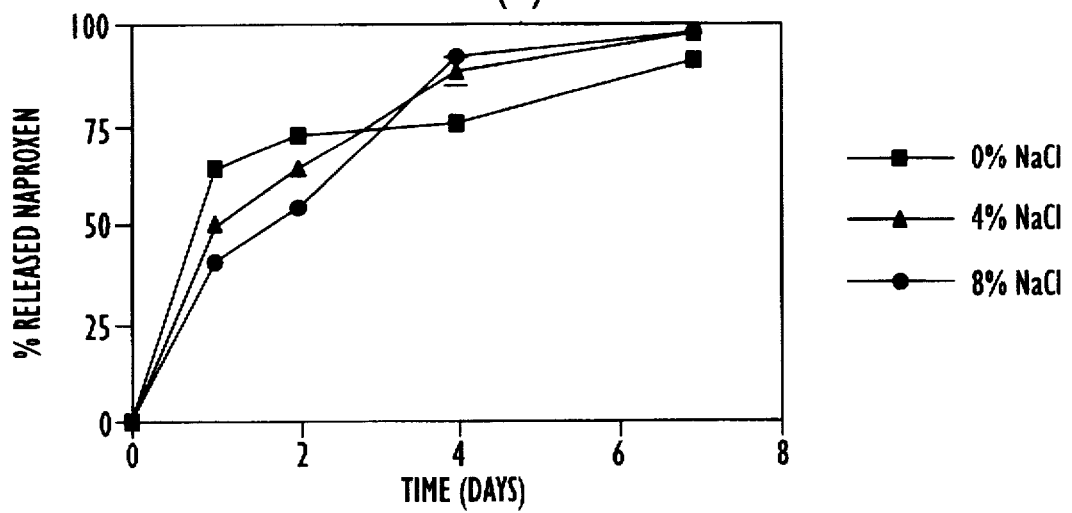

The release profiles of naproxen from the PLGA cylinders (MW=10,000) with TDBAC and sodium chloride are shown in FIGS. 2 (A) and (B), respectively. Naproxen release in excess of 90% from every cylinder illustrated in FIG. 2 was observed over 7 days. However, the naproxen release profile was affected by the additive used. Although an initial burst release of 64t of naproxen was seen for the PLGA cylinder without additive, by the addition of TDBAC at 2% and 4%, the PLGA cylinders showed complete and constant release of naproxen, independent of TDBAC content. While high initial burst release of naproxen was observed for the PLGA cylinders with sodium chloride (4% and 8%) also, the subsequent release was also accelerated and the total percentage of naproxen released over 4 days was about 90%. It is believed that the addition of sodium chloride increased the permeability of the PLGA matrices by forming aqueous pores for the low molecular weight compound.

EXAMPLE 3

This Example demonstrates that quaternary ammonium surfactants can modify the release profile of low molecular weight, water soluble drugs from PLGA matrices.

Cylinders containing 4% by weight ketorolac tromethamine (Syntex, Palo Alto, Calif.) in PLGA-18,000 without additive and with (by weight) 2% TDBAC, 4% TDBAC, 4% NaCl, or 8% NaCl were prepared as described below. A mixture (200 mg) of drug with PLGA and the selected amount of surfactant was placed in a glass tube and heated at a melt temperature of 95° C. to melt the polymer. The melt was mixed homogeneously, charged into a polypropylene syringe and extruded. A cylinder 1.3 mm in diameter was obtained, cut into 5 mm lengths, and the drug content and the molecular weight of PLGA determined to confirm their stabilities during the preparation process, by high performance liquid chromatography (HPLC), as described below. The recovery of ketorolac from the cylinder was more than 90% and the molecular weight of the PLGA remained unaltered.

Ketorolac was extracted from the PLGA cylinder in a mixed solution of acetonitrile and potassium phosphate aqueous solution (23:77) and assayed by HPLC, column: Spherisorb C18, 4.6 mm×25 cm; mobile phase: $CH_3OH$—$H_2O$—$CH_3COOH$ (55:44:1); flow rate: 0.8 ml/min.; wavelength: 254 nm.

Drug release properties were studied at 37° C. using a rotating bottle apparatus. A cylinder was put into a glass bottle containing 5 ml of 0.2M phosphate buffer, pH 7.0. The medium was replaced by a fresh one at specified times and analyzed for the released drug by HPLC under the same conditions as described above.

Figure 3A:
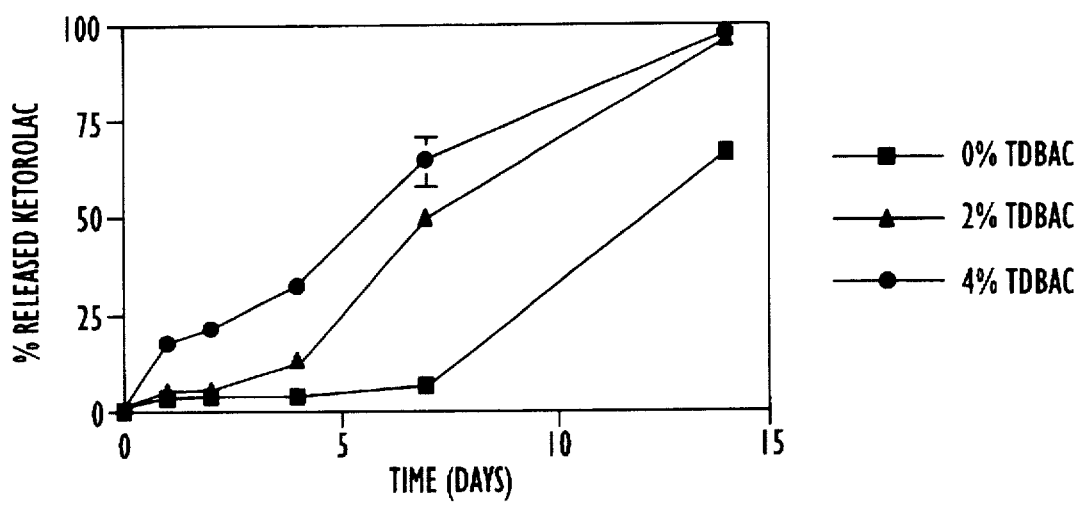
FIG. 3 Cumulative release profile of keterolac tromethamine from PLGA cylinders, with (A) TDBAC or (B) NaCl.
Figure 3B:
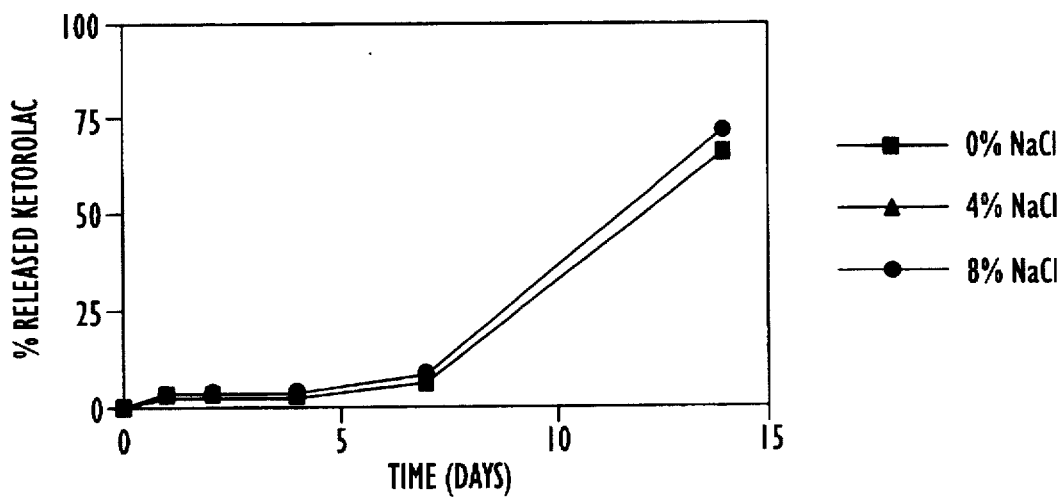

FIG. 3 illustrates the release profiles of ketorolac from the PLGA cylinders (MW=18,000) with TDBAC and sodium chloride; (A): TDBAC and (B): sodium chloride, respectively. In spite of the low molecular weight and high solubility in water, a lag time with little drug release was shown for the PLGA cylinder without additive. After the lag time of 7 days, a rapid release of ketorolac was observed for the following 7 days and reached about 70%. In the cylinders with additive, while sodium chloride showed no effect on the ketorolac release, the lag time in the release profile decreased with increasing amounts of TDBAC and the release rates became more constant until the completion of the release. The results indicate that the high molecular weight (18,000) PLGA matrix was too dense for adequate penetration of water, but its permeability was improved by the addition of TDBAC.

The foregoing Examples are presented for illustrative purposes only and should not be construed as limiting the invention in any way.

What is claimed is:

1. A sustained release composition comprising a poly (lactic/glycolic) acid copolymer, a bioactive agent, and a quaternary ammonium surfactant.

2. A composition of claim 1 wherein the quaternary ammonium ion of said surfactant is selected from the group consisting of alkylammonium, benzalkonium, and pyridinium ions.

3. A composition of claim 2 wherein the quaternary ammonium ion is selected from the group consisting of alkyltrimethylammonium, alkyldimethylbenzylammonium, and alkylpyridinium and alkylimidazolium ions.

4. A composition of claim 3 wherein the quaternary ammonium ion is selected from tetradecyldimethylbenzylammonium and cetylpyridinium.

5. A composition of claim 1 wherein the molar ratio of lactic/glycolic acid in said poly(lactic/glycolic acid) polymer is about 100:0 about 25:75.

6. A composition of claim 1 wherein said poly(lactic/glycolic acid) polymer has a weight average molecular weight of about 4,500 to about 50,000.

7. A composition of claim 6 wherein said poly(lactic/glycolic acid) polymer has a weight average molecular weight of about 4,500 to about 18,000.

8. A composition of claim 1 wherein said quaternary ammonium surfactant comprises from about 0.5 to about 15 percent by weight of the composition.

9. A composition of claim 8 wherein said quaternary ammonium surfactant comprises from about 2 to about 8 percent by weight of the composition.

10. A composition of claim 1 wherein said bioactive agent comprises from about 0.1 to about 20 percent by weight of the composition.

11. A composition of claim 10 wherein said bioactive agent comprises from about 1 to about 10 percent by weight of the composition.

12. A composition of claim 11 wherein said bioactive agent comprises from about 2 to about 6 percent by weight of the composition.

13. A sustained release composition comprising:

a) a poly(lactic/glycolic) acid copolymer; b) a bioactive agent selected from the group consisting of nafarelin, naproxen, and ketorolac; c) a quaternary ammonium surfactant.

14. A composition of claim 13 wherein the quaternary ammonium ion of said surfactant is selected from the group consisting of alkylammonium, benzalkonium, and pyridinium ions.

15. A composition of claim 14 wherein the quaternary ammonium ion is selected from the group consisting of alkyltrimethylammonium, alkyldimethylbenzylammonium, and alkylpyridinium and alkylimidazolium ions.

16. A composition of claim 15 wherein the quaternary ammonium ion is selected from tetradecyldimethylbenzylammonium and cetylpyridinium.

* * * * *